US010585052B2

(12) United States Patent
Chen et al.

(10) Patent No.: US 10,585,052 B2
(45) Date of Patent: Mar. 10, 2020

(54) SECURITY INSPECTION APPARATUS AND METHOD

(71) Applicant: NUCTECH COMPANY LIMITED, Beijing (CN)

(72) Inventors: Zhiqiang Chen, Beijing (CN); Ziran Zhao, Beijing (CN); Jin Cui, Beijing (CN); Dong Lin, Beijing (CN); Bin Hu, Beijing (CN); Xianshun Tan, Beijing (CA); Hong Wang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 116 days.

(21) Appl. No.: 15/609,012

(22) Filed: May 31, 2017

(65) Prior Publication Data
US 2018/0038808 A1 Feb. 8, 2018

(30) Foreign Application Priority Data

Aug. 5, 2016 (CN) .......................... 2016 1 0634086

(51) Int. Cl.
G01N 23/00 (2006.01)
G01N 23/203 (2006.01)
G01V 5/00 (2006.01)

(52) U.S. Cl.
CPC ......... *G01N 23/203* (2013.01); *G01V 5/0025* (2013.01)

(58) Field of Classification Search
CPC ...... G01N 23/00; G01N 23/04; G01N 23/203; A61B 6/483; A61B 6/58; A61B 6/588; A61B 6/589
(Continued)

(56) References Cited

U.S. PATENT DOCUMENTS 5,022,062 A * 6/1991 Annis ................. G01N 23/203
378/57
6,967,612 B1 11/2005 Gorman et al.
(Continued)

FOREIGN PATENT DOCUMENTS

CN 1556921 A 12/2004
CN 101162205 A 4/2008
(Continued)

OTHER PUBLICATIONS

Dinca Dan Cristian et al: "Rapid inspection of general aviation aircraft for security threats and contraband", 2014 International Carnahan Conference on Security Technology (ICCST), IEEE, Oct. 13, 2014, pp. 1-5, XP032705697, DOI: 10.1109/CCST.2014. 6987006, ISBN: 978-1-4799-3530-7, retrieved on Dec. 15, 2014, 5 pages.

(Continued)

Primary Examiner — Jurie Yun
(74) Attorney, Agent, or Firm — Kilpatrick Townsend & Stockton LLP

(57) ABSTRACT

The present disclosure proposes a security inspection apparatus and method, relates to the technical field of radiation, wherein the security inspection apparatus of the disclosure includes: radiation emitting device, back-scatter detector, size-distance detecting device, orientation adjusting device; the back-scatter detector located between the radiation emitting device and an inspected object; the size-distance detecting device located between the radiation emitting device and the inspected object, for detecting a size of the inspected object and/or a distance between the inspected object and the size-distance detecting device; and the orientation adjusting device adjusts orientation of the radiation emitting device according to the size of the inspected object and/or the distance from the inspected object.

19 Claims, 8 Drawing Sheets

(58) Field of Classification Search
USPC .............. 378/57, 70, 86, 87, 162, 205, 207
See application file for complete search history.

(56) References Cited

U.S. PATENT DOCUMENTS

| | | | |
|---|---|---|---|
| 8,734,013 B2 * | 5/2014 | Singh .................. | G01N 23/043 378/146 |
| 2004/0086078 A1 | 5/2004 | Adams et al. | |
| 2010/0189226 A1 | 7/2010 | Kotowski et al. | |
| 2013/0101090 A1 * | 4/2013 | Schubert ............. | G01N 23/203 378/87 |
| 2014/0226789 A1 | 8/2014 | Bendahan et al. | |

FOREIGN PATENT DOCUMENTS

| | | | |
|---|---|---|---|
| CN | 104062688 | A | 9/2014 |
| CN | 104133251 | A | 11/2014 |
| CN | 105301669 | A | 2/2016 |
| CN | 205879830 | U | 1/2017 |
| EP | 1970700 | A1 | 9/2008 |
| EP | 2963454 | A1 | 1/2016 |
| WO | 2005121756 | A2 | 12/2005 |
| WO | 2012142453 | A2 | 10/2012 |

OTHER PUBLICATIONS

EP Official Communication dated Jul. 1, 2019 in the corresponding EP application (application No. 17173471.8).

* cited by examiner

SECURITY INSPECTION APPARATUS AND METHOD

TECHNICAL FIELD

The present disclosure relates to the technical field of radiation, and particularly a security inspection apparatus and method.

BACKGROUND ART

X-ray backscatter imaging is getting more and more important in security inspection because it can well detect the material of an object with a low atomic number. An embodiment is as follows: a flywheel rotates about a radiation source to form a pencil beam, and the pencil beam interacts with an inspected object to form a flying spot through Compton scattering. A back-scatter detector collects X-ray backscatter rays of the flying spot at any time, and after processing, information of the material is obtained, i.e., a backscatter image is formed. After continuous scanning, internal information of the whole object inspected can be processed and obtained, and objects with a lower atomic number, e.g., contraband goods such as explosives, drugs, hidden in concealed locations such as vehicle door interlayer, vehicle bottom, could be highlighted.

The existing flying point device operates as follows: a radiation source generates fan-shaped X-rays that pass through a rotating shield with multiple collimating holes to continuously generate a pencil beam for achieving a first dimensional scanning, and achieving a second-dimensional scanning by rotating or translating the rays to scan sectors.

However, if objects with different sizes are lined up, and the existing backscatter device is stationary in its scanning angle and scanning position including vertical and horizontal position, the view angle of the image is possibly bad, such that occlusion or overlap is formed between internal structures of the inspected objects, and suspicious goods cannot be highly identified under this angle.

SUMMARY OF THE DISCLOSURE

An object of this disclosure is to provide a security inspection approach that can flexibly adjust the position of the ray source according to the condition of the inspected object.

According to an aspect of the disclosure, a security inspection apparatus is provided, comprising: a radiation emitting device, a back-scatter detector located between the radiation emitting device and an inspected object, a size-distance detecting device located between the radiation emitting device and the inspected object, for detecting a size of the inspected object and/or a distance from the inspected object, and an orientation adjusting device for adjusting a orientation of the radiation emitting device according to the size of the inspected object and/or the distance between the inspected object and the size-distance detecting device.

Further, the orientation adjusting device further adjusts an angle of the back-scatter detector according to the orientation of the radiation emitting device.

Further, the size-distance detecting device comprises a plurality of sensors for determining a height of the inspected object by judging a height of an obstacle in front of the sensors.

Further, the size-distance detecting device further comprises: a camera located on a perpendicular bisector of the security inspection apparatus and the inspected object in a horizontal plane, and shoots in the direction of the perpendicular bisector; a calculating device acquires an image height of the inspected object and an image distance between the inspected object and the size-distance detecting device in a video image shot by the camera, and determines a distance between the inspected object and the size-distance detecting device from a ratio of the image distance to the image height and the height of the inspected object detected by the sensor.

Further, the orientation adjusting device adjusts a height and an emission angle of the radiation emitting device based on a predetermined gear, according to the height of the inspected object and/or the distance between the inspected object and the size-distance detecting device.

Further, the orientation adjusting device adjusts a distance between the radiation emitting device and the inspected object based on a predetermined gear, according to the height of the inspected object and/or the distance between the inspected object and the size-distance detecting device.

Further, the orientation adjusting device determines an ideal height and an ideal emission angle of the radiation emitting device based on a predetermined strategy, from the height of the inspected object and/or the distance between the inspected object and the size-distance detecting device, and adjusts the height and the emission angle of the radiation emitting device according to the ideal height and the ideal emission angle.

Further, the orientation adjusting device determines an ideal distance between the radiation emitting device and the inspected object based on a predetermined strategy, from the height of the inspected object and/or the distance between the inspected object and the size-distance detecting device, and adjusts the distance between the radiation emitting device and the inspected object according to the ideal distance.

Further, the orientation adjusting device adjusts an angle of the back-scatter detector based on a predetermined gear, according to the height and the emission angle of the radiation emitting device, or determines an ideal angle of the back-scatter detector from the height and the emission angle of the radiation emitting device, and adjusts the angle of the back-scatter detector according to the ideal angle.

Further, the back-scatter detector is arc-shaped.

Further, the radiation emitting device comprises: a ray source located in a center of the radiation emitting device; and a spatial modulator located between the radiation source and the back-scatter detector, comprising a fixed shielding plate and a rotating shielding plate which located between the inspected object and the fixed shielding plate, and comprises more than one hole.

Further, the security inspection apparatus further comprises a transportation facility for carrying and moving the security inspection apparatus.

Further, the security inspection apparatus further comprises: a control device for manually controlling the orientation adjusting device to perform the adjusting operation according to detection needs.

Further, the security inspection apparatus further comprises a processor for receiving detection signals from the back-scatter detector.

Such a security inspection apparatus can detect size and position information of the inspected object, and automatically adjust the orientation of the radiation emitting device according to the size and position of the inspected object, thereby reducing or avoiding detection dead angles, and improving accuracy of the detection.

According to another aspect of the disclosure, a security inspection method is provided, comprising: acquiring a height of an inspected object and a distance between the inspected object and a size-distance detecting device; adjusting an orientation of a radiation emitting device according to the height of the inspected object and the distance between the inspected object and the size-distance detecting device; acquiring backscatter detection data by a back-scatter detector; and acquiring a detection result based on the backscatter detection data.

Further, the security inspection method further comprise: adjusting an angle of the back-scatter detector according to the orientation of the radiation emitting device.

Further, acquiring a height of an inspected object comprises: the height of the inspected object is acquired by using a plurality of sensors acquire to judge a height of an obstacle in front of the sensors.

Further, acquiring a distance between the inspected object and the size-distance detecting device comprises: a video image is acquired by using a camera located on a perpendicular bisector of the security inspection apparatus and the inspected object in a horizontal plane, and shooting in the direction of the perpendicular bisector; acquiring an image height of the inspected object and an image distance between the inspected object and the size-distance detecting device in the video image, and determining a distance between the inspected object and the size-distance detecting device from a ratio of the image distance to the image height and the height of the inspected object.

Further, adjusting the orientation of the radiation emitting device according to the height of the inspected object and the distance between the inspected object and the size-distance detecting device further comprises: adjusting a height and a emission angle of the radiation emitting device based on a predetermined gear, according to the height of the inspected object and/or the distance between the inspected object and the size-distance detecting device.

Further, adjusting the orientation of the radiation emitting device according to the height of the inspected object and the distance between the inspected object and the size-distance detecting device further comprises: adjusting the distance between the radiation emitting device and the inspected object based on a predetermined gear, according to the height of the inspected object and the distance between the inspected object and the size-distance detecting device.

Further, adjusting the orientation of the radiation emitting device according to the height of the inspected object and the distance between the inspected object and a size-distance detecting device further comprises: determining an ideal height and an ideal emission angle of the radiation emitting device based on a predetermined strategy, from the height of the inspected object and/or the distance between the inspected object and the size-distance detecting device, and adjusting the height and the emission angle of the radiation emitting device according to the ideal height and the ideal emission angle.

Further, adjusting the orientation of the radiation emitting device according to the height of the inspected object and the distance between the inspected object and a size-distance detecting device further comprises: determining an ideal distance between the radiation emitting device and the inspected object using a predetermined strategy from the height of the inspected object and/or the distance between the inspected object and a size-distance detecting device, and adjusting the distance between the radiation emitting device and the size-distance detecting device according to the ideal distance.

Further, adjusting an angle of the back-scatter detector according to the orientation of the radiation emitting device further comprises: adjusting the angle of the back-scatter detector based on a predetermined gear, according to the height and the emission angle of the radiation emitting device.

Further, adjusting an angle of the back-scatter detector according to the orientation of the radiation emitting device further comprises: determining an ideal angle of the back-scatter detector from the height and the emission angle of the radiation emitting device, and adjusting the angle of the back-scatter detector according to the ideal angle.

Further, the security inspection method further comprise: manually adjusting the orientation of the radiation emitting device and/or the angle of the back-scatter detector according to detection needs.

Further, manually adjusting the orientation of the radiation emitting device and/or the angle of the back-scatter detector according to detection needs comprises: manually adjusting the orientation of the radiation emitting device and/or the angle of the back-scatter detector for many times according to detection needs; acquiring backscatter detection data by a back-scatter detector comprises acquiring backscatter detection data after each time adjusting the orientation of the radiation emitting device and the angle of the back-scatter detector; and acquiring a detection result based on the backscatter detection data comprises: making a comprehensive analysis of the backscatter detection data acquired each time to determine the detection result.

In this way, we can detect size and position information of the inspected object, and automatically adjust the orientation of the radiation emitting device according to the size and position of the inspected object, thereby reducing or avoiding detection dead angles, and improving accuracy of the detection.

BRIEF DESCRIPTION OF THE ACCOMPANYING DRAWINGS

The accompanying drawings illustrated herein provide further understandings to the disclosure and constitute a portion of the present application. The illustrative embodiments of the disclosure and their descriptions are used for explaining the disclosure and do not constitute improper definitions to the disclosure.

DETAILED DESCRIPTION OF THE PREFERRED EMBODIMENTS

The present disclosure will be further illustrated below in details in conjunction with the accompanying drawings with exemplary embodiments. It is to be understood that the following Detailed Description is merely exemplary, rather than to limiting the present disclosure inappropriately.

The existing X-ray inspection apparatus cannot make real-time adjustments according to the size and position of the inspected object since components thereof have relatively fixed positions, which possibly will result in a poor effect of the backscatter scan image: for example, if the ray emission position is fixed, the view angle of the output image perhaps will be bad, and internal structures form occlusion or overlap, and suspicious objects cannot be well identified.

Figure 1:
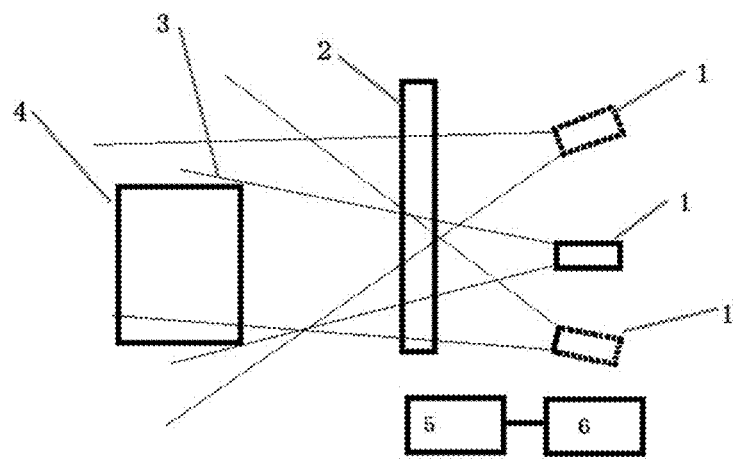
FIG. 1 is a schematic diagram of the security inspection apparatus according to one embodiment of this disclosure.

FIG. 1 is a schematic diagram of the security inspection apparatus according to one embodiment of this disclosure. The radiation emitting device 1 is capable of emitting rays 3 to an inspected object 4. The back-scatter detector is capable of acquiring backscatter rays and generating backscatter data. The security inspection apparatus further comprises a size-distance detecting device 5 located between the radiation emitting device 1 and the inspected object 4. The size-distance detecting device 5 is capable of detecting a size of the inspected object 4 and a distance from the inspected object 4. The orientation adjusting device 6 is capable of adjusting the orientation of the radiation emitting device according to the size of the inspected object 4 and the distance between the inspected object 4 and the size-distance detecting device 5. As shown by the dotted lines in FIG. 1, the orientation adjusting device can adjust height, emission angle, and etc. of the radiation emitting device. For example, when it is detected that the inspected object is high, reduce the height of the radiation emitting device, and emit ray beams at an angle horizontally upwards; when it is detected that the inspected object is low, raise the height of the radiation emitting device, and emit ray beams at an angle horizontally downwards; when it is detected that the distance between the inspected object and the size-distance detecting device is fare, the decrease the distance between the radiation emitting device and the size-distance detecting device; when it is detected that the distance between the inspected object and the size-distance detecting device is near, increase the distance between the radiation emitting device and the size-distance detecting device.

Such a security inspection apparatus can detect size and position information of the inspected object, and automatically adjust the orientation of the radiation emitting device according to the size and position of the inspected object, thereby reducing or avoiding detection dead angles, and improving accuracy of the detection.

In an embodiment, the back-scatter detector may be arc-shaped, and such a security inspection apparatus can better receive backscatter rays to thereby generate better backscatter data.

Figure 2:
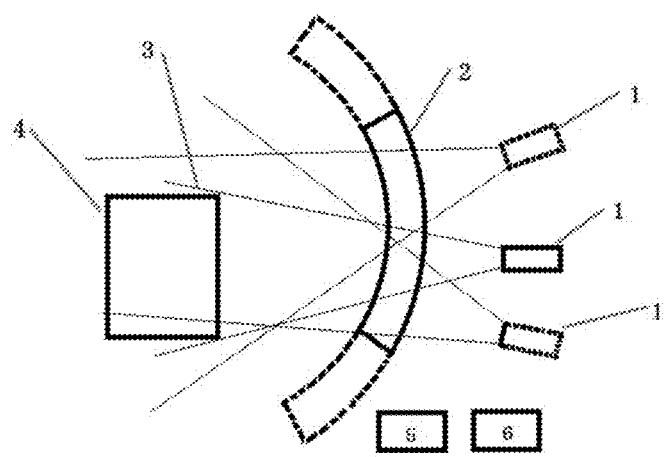
FIG. 2 is a schematic diagram of the security inspection apparatus according to another embodiment of this disclosure.

In one embodiment, the orientation adjusting device can adjust the angle of the back-scatter detector according to the orientation of the radiation emitting device. As shown in FIG. 2, when the radiation emitting device 1 is adjusted to the orientation of the radiation emitting device 1 shown by the dotted lines on top of the figure, the back-scatter detector is adjusted to an angle of the back-scatter detector 2 shown by the dotted lines in a lower portion; when the radiation emitting device 1 is adjusted to the orientation of the radiation emitting device 1 shown by the dotted lines on the bottom of the figure, the back-scatter detector is adjusted to an angle of the back-scatter detector 2 shown by the dotted lines in a upper portion; when the radiation emitting device 1 is in the position shown by the middle solid lines, the back-scatter detector is adjusted to an angle of the back-scatter detector 2 drawn by the middle solid lines.

Such a security inspection apparatus can adjust the orientation of the radiation emitting device according to the position and size of the inspected object, and can adjust the angle of the back-scatter detector according to the orientation of the radiation emitting device, thereby better receiving backscatter rays to acquire more accurate and complete backscatter data.

Figure 3:
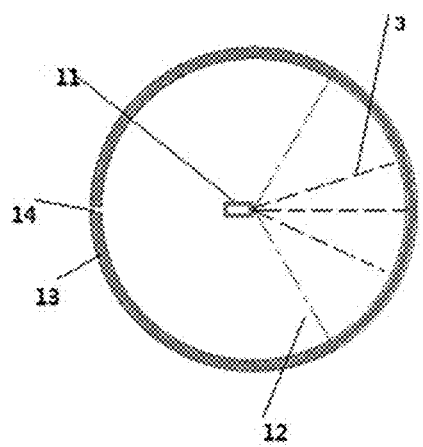
FIG. 3 is a schematic diagram of the radiation emitting device of the security inspection apparatus according to one embodiment of this disclosure.

In one embodiment, a schematic diagram of the radiation emitting device 1 of the security inspection apparatus is shown in FIG. 3. A ray source 11 can emits X-rays 3; a fixed shielding plate 12 is capable of restricting the rays 3 to be emitted in a fixed direction with a fixed angle; a rotating shield 13 has at least one hole 14. The rotating shield 13 rotates continuously, and when the hole 14 reaches the emission range of the rays 3 restricted by the fixed shielding plate 12, the rays are emitted through the hole 14 to form a flying spot beam.

In such a security inspection apparatus, the radiation emitting device can emit rays with a predetermined frequency and angle, which facilitates adjustment and control as needed.

In one embodiment, the size-distance detecting device comprises a plurality of sensors for determining a height of the inspected object by judging a height of an obstacle in front of the sensors. In one embodiment, the size-distance detecting device has a column of sensors that can judge a height of the inspected object by judging that in front of which sensors there are obstacles.

Such a security inspection apparatus can determine the size of the inspected object by existed and easily assembled equipments, and thus has a low cost and is easily promoted and applied.

Figure 4:
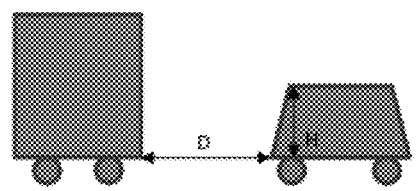
FIG. 4 is a schematic diagram showing the security inspection apparatus determines a distance between the inspected object and the size-distance detecting device from one embodiment of this disclosure.

In an embodiment, there is a camera located on a perpendicular bisector of the security inspection apparatus and the inspected object in horizontal plane, which shoots in the direction of the perpendicular bisector, and thus can acquire a video image of the inspected object. An embodiment of the view angle of the video image is shown in FIG. 4. Based on the video image, an image distance d between the inspected object and the size-distance detecting device, and an image height h of the inspected object can be acquired. Since the sensor can be utilized for acquiring an actual height H of the inspected object, as shown in FIG. 4, the object on the left side is the security inspection apparatus, and the object on the right side is the inspected object. The actual distance between the inspected object and the size-distance detecting device is D. The actual distance D between the inspected object and the camera is determined from the formula:

$$D=(dH)/h,$$

It can be regard as the distance between the inspected object and the size-distance detecting device.

Such a security inspection apparatus can acquire the size of the inspected object, and the distance from the size-distance detecting device by cleverly using the sensors and the camera in combination with data analysis, thereby providing data for adjusting the orientation of the radiation emitting device and the angle of the back-scatter detector.

In one embodiment, there is a 3D camera in the vicinity of the sensor, which can directly acquire the distance information between the inspected object and the camera. Such an apparatus has a simpler construction, and response speed of the security inspection apparatus is increased since operations of calculation are omitted.

Figure 5:
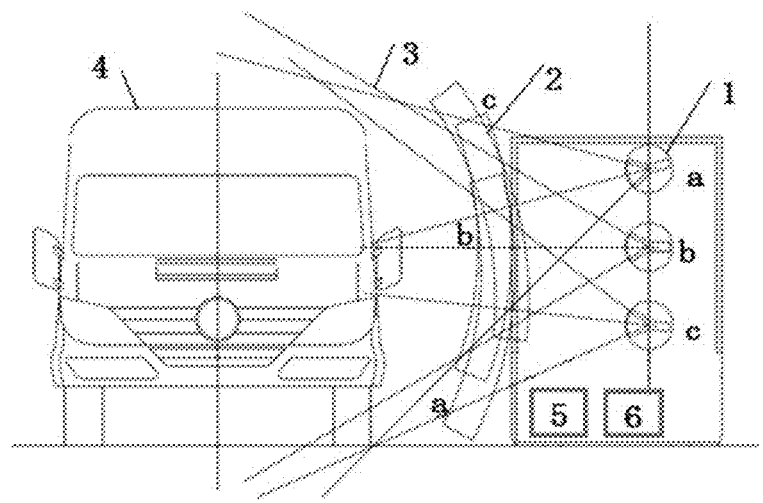
FIG. 5 is a schematic diagram of the security inspection apparatus according to a further embodiment of this disclosure.

In one embodiment, a plurality of gears can be set according to actual size requirements of the inspected object, each gear for detecting inspected objects in a corresponding predetermined size range. In an embodiment, the inspected object may be a vehicle. Since the size of vehicles is relatively fixed, and can be classified as three kinds, namely full size vehicle, midsize vehicle and compact size vehicle, the gears of the radiation emitting device 1 and the back-scatter detector 2 can be set according to the vehicle's size. As shown in FIG. 5, three gears a, b, c can be set, wherein the gear b is a reference gear in which the radiation emitting device is in the middle and shoots in the horizontal direction; the radiation emitting device at the gear a is located about 60 cm above the reference gear position and emits rays horizontally downwards at a 30 degree angle; the radiation emitting device at the gear c is located about 60 cm under the reference gear position, and emits rays horizontally upwards at a 30 degree angle.

A compact size vehicle can use the gear a, a midsize vehicle can use the gear b, and a full size vehicle can use the gear c. The position and angle of the radiation emitting device 1 and the back-scatter detector 2 at respective gears can be determined from the size of the inspected vehicle. Such a security inspection apparatus can adjust the orientation of the radiation emitting device and the angle of the back-scatter detector according to the predetermined gears, and thus has advantages such as lower requirement on the apparatus, faster response speed, and is easily promoted and applied.

In an embodiment, after acquiring the height of the inspected object, and the distance between the size-distance detecting device and the inspected object, an ideal height of the radiation emitting device and an ideal emission angle can be calculated based on a predetermined strategy, and the radiation emitting device can be adjusted to be in the ideal height, and emit rays with the ideal angle. Such a security inspection apparatus is adapted to the detection of various sizes of the inspected objects, and can adjust the radiation emitting device according to the ideal height and angle to detect the inspected object, thereby obtaining more accurate detection data and reaching a better detection effect.

In an embodiment, a plurality of gears can also be set for the distance between the radiation emitting device and the size-distance detecting device to adjust the horizontal orientation of the radiation emitting device. Since viewed from the principle of back-scatter detection, the closer the radiation emitting device is to the inspected object, the better the effect is. However, since the radiation angle of the radiation emitting device is limited, the distance between the radiation emitting device and the inspected object should be closer under the premise that the radiation angle covers the area to be inspected, and this distance is the ideal detection distance between the radiation emitting device and the inspected object.

If the ideal detection distance between the radiation emitting device and the inspected object is D1, and the distance between the size-distance detecting device and the inspected object is D, then the ideal distance between the radiation emitting device and the size-distance detecting device is D1–D, so a gear in which the distance between the radiation emitting device and the size-distance detecting device is closest to D1–D is selected, and the radiation emitting device is adjusted to the corresponding gear position. For example, three gears a, b, c are set for the distance between the radiation emitting device and the size-distance detecting device, the distance between the radiation emitting device and the size-distance detecting device is 45 cm, 60 cm, 75 cm respectively. According to the size of the inspected object, it is determined that the ideal distance between the inspected object and the radiation emitting device is 2 m, and the distance between the inspected object and the size-distance detecting device is 1.5 m, so it is needed to adjust the distance between the size-distance detecting device and the radiation emitting device to be 50 cm, then the radiation emitting device is adjusted to be in the position of gear a.

Such a security inspection apparatus can adjust the distance between the radiation emitting device and the size-distance detecting device according to the distance between the inspected object and the size-distance detecting device, realize the adjustment of the distance between the radiation emitting device and the inspected object, which on one hand, optimizes the detection effect, and on the other hand, reduces the requirement on the distance between the security inspection apparatus and the inspected object, such that the security inspection process is more convenient and feasible.

In an embodiment, it can be calculated according to the ideal detection distance D1 between the radiation emitting device and the inspected object, and the distance D between the size-distance detecting device and the inspected object that, the ideal distance between the radiation detecting device and the size-distance detecting device is D1–D, thereby adjusting the distance between the radiation emitting device and the size-distance detecting device as the ideal distance. For example, it is determined according to the size of the inspected object that the ideal distance between the inspected object and the radiation emitting device is 2 m, and the distance between the inspected object and the size-distance detecting device is 1.5 m, so it is needed to adjust the distance between the radiation emitting device and the size-distance detecting device to be 50 cm, and then the radiation emitting device is adjusted to be located at a distance of 50 cm from the size-distance detecting device.

Such a security inspection apparatus can adjust the orientation of the radiation emitting device according to the ideal distance between the radiation emitting device and the size-distance detecting device, which further optimizes the detection effect.

Figure 6:
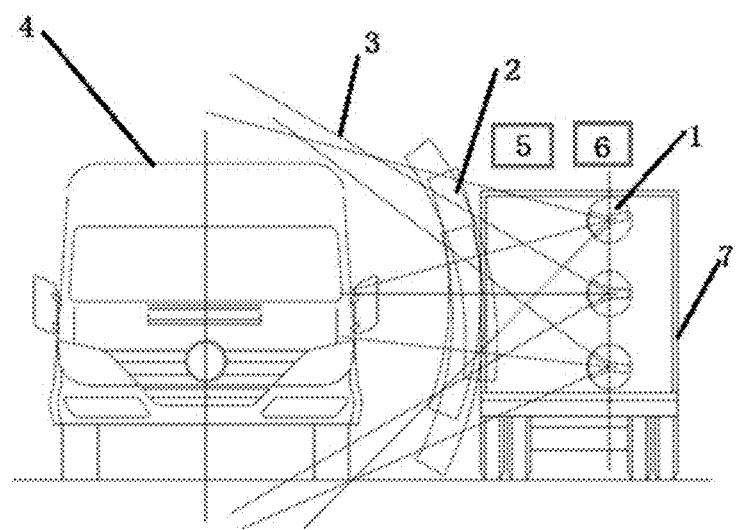
FIG. 6 is a schematic diagram of the security inspection apparatus according to a further again embodiment of this disclosure.

FIG. 6 is a schematic diagram showing the security inspection apparatus according to a further again embodiment of the disclosure. The security inspection apparatus further comprises a transportation facility 7 for carrying and moving the security inspection apparatus, which has the following advantages: facilitating transportation and flexible scheduling directed to emergencies; occupying a smaller area; continuously detecting a plurality of inspected objects by moving the security inspection apparatus in case where the inspected objects are inconvenient to be moved; easy use and convenient promotion and application.

In one embodiment, the security inspection apparatus further comprises a processor for receiving detection signals from the back-scatter detector, generating backscatter detection images, analyzing the inspected object and generating the detection result. Such a security inspection apparatus can obtain the detection image and the detection result in real time, which improves the detection efficiency.

In one embodiment, the security inspection apparatus further comprises a control device. An operator can manually adjust the position of the radiation detecting device and the angle of the back-scatter detector with the control device. By using such a security inspection apparatus, the operator can adjust the radiation detecting device and the back-scatter detector from multiple angles and positions according to detection needs, which is helpful to the identification of suspicious objects and improves accuracy of the detection.

Figure 7:
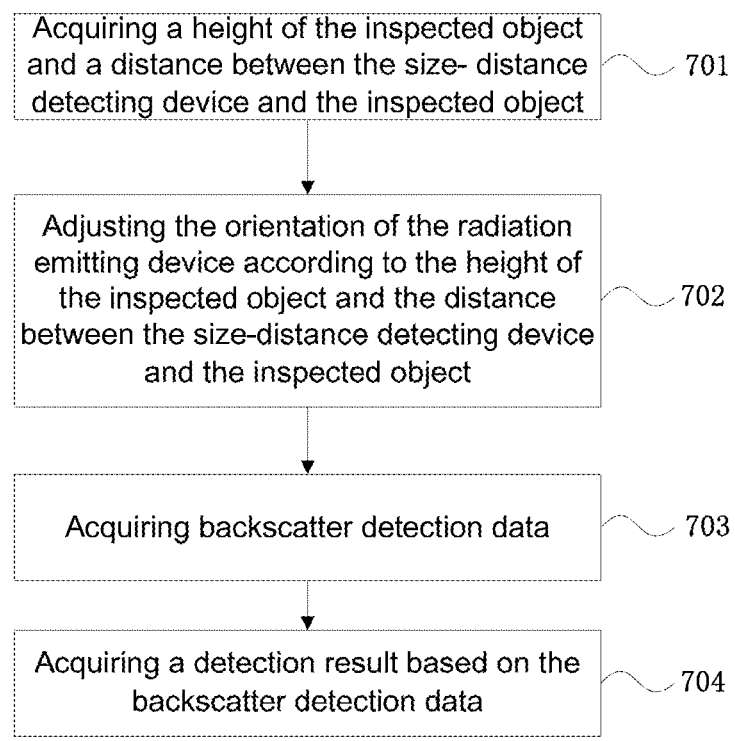
FIG. 7 is a flowchart showing the security inspection method according to an embodiment of this disclosure.

FIG. 7 is a flowchart showing the security inspection method according to an embodiment of the disclosure.

In step 701, the size-distance detecting device acquires a height of the inspected object and a distance between the inspected object and the size-distance detecting device.

In step 702, the orientation of the radiation emitting device is adjusted according to the height of the inspected object and the distance between the inspected object and the size-distance detecting device. For example, when it is detected that the inspected object is high, reduce the height of the radiation emitting device, and emit ray beams at an angle horizontally upwards; when it is detected that the inspected object is low, raise the height of the radiation emitting device, and emit ray beams at an angle horizontally downwards; when it is detected that the distance between the inspected object and the size-distance detecting device is fare, the decrease the distance between the radiation emitting device and the size-distance detecting device; when it is detected that the distance between the inspected object and the size-distance detecting device is near, increase the distance between the radiation emitting device and the size-distance detecting device.

In step 703, the backscatter detection data is acquired by using a back-scatter detector.

In step 704, a detection result is acquired based on the backscatter detection data.

In this way, we can detect size and position information of the inspected object, and automatically adjust the orientation of the radiation emitting device according to the size and position of the inspected object, thereby reducing or avoiding detection dead angles, and improving accuracy of the detection.

Figure 8:
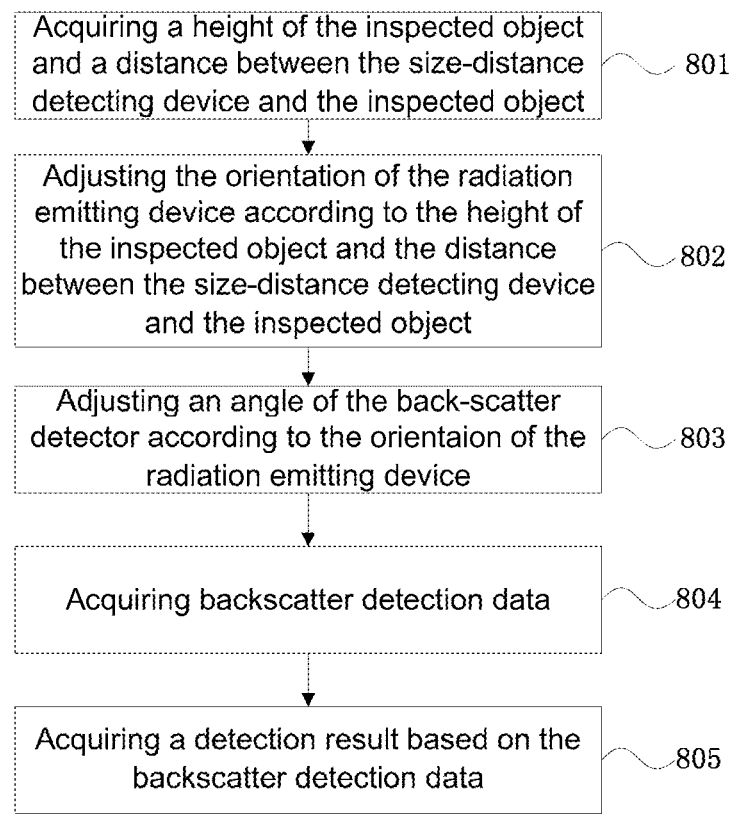
FIG. 8 is a flowchart showing the security inspection method according to another embodiment of this disclosure.

FIG. 8 is a flowchart showing the security inspection method according to another embodiment of the disclosure.

In step 801, a height of the inspected object and a distance between the inspected object and the size-distance detecting device are acquired by using a size-distance detecting device.

In step 802, the orientation of the radiation emitting device is adjusted according to the height of the inspected object, and the distance between the inspected object and the size-distance detecting device.

In step 803, an angle of the back-scatter detector is adjusted according to the orientation of the radiation emitting device. As shown in FIG. 2, when the radiation emitting device 1 is adjusted to the orientation of the radiation emitting device 1 shown by the dotted lines on top of the figure, the back-scatter detector is adjusted to an angle of the back-scatter detector 2 shown by the dotted lines in a lower portion; when the radiation emitting device 1 is adjusted to the orientation of the radiation emitting device 1 shown by the dotted lines on the bottom of the figure, the back-scatter detector is adjusted to an angle of the back-scatter detector 2 shown by the dotted lines in a upper portion; when the radiation emitting device 1 is in the position shown by the middle solid lines, the back-scatter detector is adjusted to an angle of the back-scatter detector 2 drawn by the middle solid lines.

In step 804, backscatter detection data is acquired by using a back-scatter detector.

In step 805, a detection result is acquired based on the backscatter detection data.

In this way, we can adjust the orientation of the radiation emitting device according to the position and size of the inspected object, and can adjust the angle of the back-scatter detector according to the orientation of the radiation emitting device, thereby better receiving backscatter rays to acquire more accurate and complete backscatter data.

In one embodiment, a plurality of sensors may be utilized for determining a height of the inspected object by judging a height of an obstacle in front of the sensors. In one embodiment, the size-distance detecting device has a column of sensors that can judge a height of the inspected object by judging that in front of which sensors there are obstacles. Such a method can determine the size of the inspected object by existed and easily assembled equipments, and thus has a low cost and is easily promoted and applied.

Figure 9:
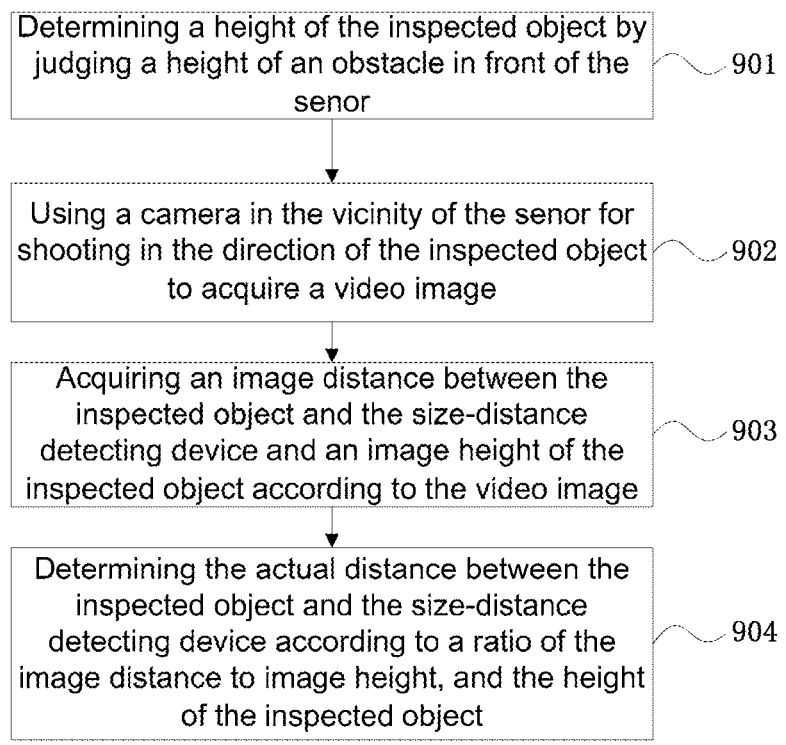
FIG. 9 is a flowchart showing one embodiment for determining a height of the inspected object and a distance between the size-distance detecting device and the inspected object according to this disclosure.

In an embodiment, a camera close to the sensor can be utilized for shooting in the direction of the inspected object, thus we can acquire a video image of the inspected object. And then a distance between the inspected object and the camera can be acquired according to the video image and the height of the inspected object determined by the sensor. As shown in FIG. 9.

In step 901, a height H of the inspected object is determined by judging a height of an obstacle in front of the sensor.

In step 902, a camera which is located on a perpendicular bisector of the security inspection apparatus and the inspected object in horizontal plane, shoots in the direction of the perpendicular bisector between the security inspection apparatus and the inspected object.

In step 903, an image height h of the inspected object and an image distance d between the inspected object and the size-distance detecting device are acquired according to the video image.

In step 904, the actual distance between the inspected object and the size-distance detecting device is D. The actual distance between the inspected object and the size-distance detecting device is determined from the formula:

$$D=(dH)/h.$$

In this way, we can acquire the size of the inspected object, and the distance from the size-distance detecting device by cleverly using the sensors and the camera in combination with data analysis, thereby providing data for adjusting the orientation of the radiation emitting device and the angle of the back-scatter detector.

In one embodiment, a plurality of gears can be set according to actual size requirements of the inspected object, each gear for detecting inspected objects in a corresponding predetermined size range. A corresponding gear can be determined from the size of the inspected object determined by the size-distance detecting device, and then the radiation emitting device is adjusted to the position and angle of the corresponding gear.

In an embodiment, the distance between the inspected object and the size-distance detecting device is D; determine the ideal distance D1 between the inspected object and the radiation emitting device based on the size of the inspected object; and the ideal distance between the radiation emitting device and the size-distance detecting device is D1–D. A gear in which the distance between the radiation emitting device and the size-distance detecting device is closest to D1–D will be selected, and the radiation emitting device will be adjusted to the position and angle of the corresponding gear. In this way, a security inspection apparatus can adjust the distance between the radiation emitting device and the size-distance detecting device according to the distance between the inspected object and the size-distance detecting device, realize the adjustment of the distance between the radiation emitting device and the inspected object, which on one hand, optimizes the detection effect, and on the other hand, reduces the requirement on the distance between the security inspection apparatus and the inspected object, such that the security inspection process is more convenient and feasible.

In an embodiment, after acquiring the height of the inspected object, and the distance between the size-distance detecting device and the inspected object, an ideal height of the radiation emitting device and an ideal emission angle can be calculated based on a predetermined strategy, and the radiation emitting device can be adjusted to be in the ideal height, and emit rays with the ideal angle. In this way, a security inspection apparatus can adjust the radiation emitting device according to the ideal height and angle to detect the inspected object, thereby obtaining more accurate detection data and reaching a better detection effect.

In an embodiment, it can be calculated according to the ideal detection distance D1 between the radiation emitting device and the inspected object, and the distance D between the size-distance detecting device and the inspected object that, the ideal distance between the radiation detecting device and the size-distance detecting device is D1–D, thereby adjusting the distance between the radiation emitting device and the size-distance detecting device as the ideal distance.

In this way, we can adjust the orientation of the radiation emitting device according to the ideal distance between the radiation emitting device and the size-distance detecting device, which further optimizes the detection effect.

Figure 10:
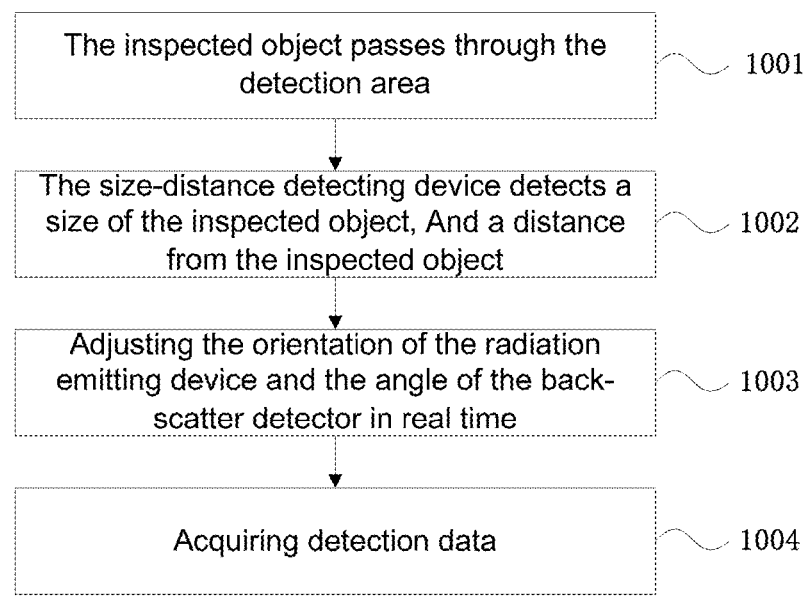
FIG. 10 is a flowchart showing the security inspection method according to a further embodiment of this disclosure.

FIG. 10 is a flowchart showing the security inspection method according to a further embodiment of the disclosure.

In a step 1001, the inspected object passes through the detection area of the security inspection apparatus.

In a step 1002, the size-distance detecting device of the security inspection apparatus detects the size of the inspected object, and a distance between the inspected object and the size-distance detecting device.

In a step 1003, the security inspection apparatus adjusts the position and angle of the radiation emitting device and the angle of the back-scatter detector according to the size of the inspected object, and the distance between the inspected object and the size-distance detecting device. The radiation emitting device emits flying point rays to the inspected object and the back-scatter detector receives the backscatter rays.

In a step 1004, detection data is acquired through the back-scatter detector. The detection image can be displayed according to the backscatter data to determine the detection result.

In this way, we can adjust the orientation of the radiation emitting device and the angle of the back-scatter detector in real time according to the size and distance from the inspected object, and achieve fast detection of the inspected object; while optimizing the detecting effect, we can continuously scan a plurality of the inspected objects, which can increase throughput of the inspected objects, improve the detection speed and guarantee the detection efficiency.

Figure 11:
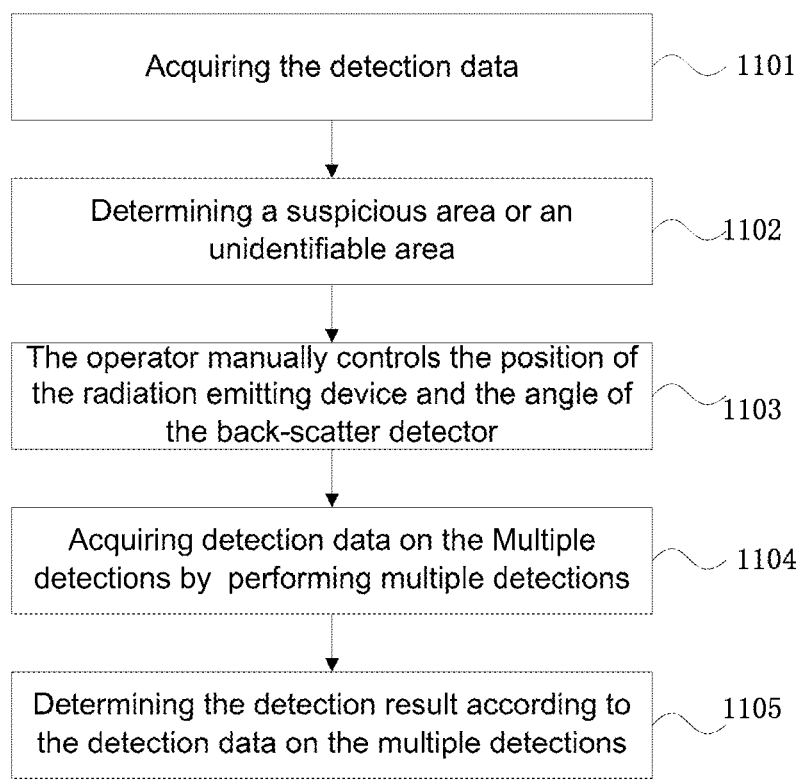
FIG. 11 is a flowchart showing the security inspection method according to a further again embodiment of this disclosure.

FIG. 11 is a flowchart of the security inspection method according to a further again embodiment of the disclosure.

In a step 1101, the detection data can be acquired in the way shown in the embodiment of FIG. 10.

In a step 1102, a suspicious area is determined from the acquired detection data. The suspicious area may comprise an unidentifiable area, a detection dead angle or a suspicious contraband object area.

In a step 1103, the operator can pay attention to the detection of the suspicious area. In an embodiment, the operator adjusts the position and angle of the radiation emitting device and the angle of the back-scatter detector, to perform multiple scans on the suspicious area.

In a step 1104, by performing multiple scans on the suspicious area, multiple detection data is acquired.

In a step 1105, determine the detection result from the multiple detection data.

In this way, we can determine the suspicious area of the inspected object from the detection data of a single rapid detection, and then adjust the position and angle of the radiation emitting device and the angle of the back-scatter detector to pay attention to the detection of the suspicious area, thereby further optimizing the detection result.

Although some particular embodiments of this disclosure have been illustrated in detail, those skilled in the art may understand that the above exemplary embodiments are merely illustrative, rather than to being any limitation to the scope of this disclosure, and various changes or modifications may be effected to above embodiments by those skilled in the art without departing from the scope and spirit of this disclosure as defined in the appended claims.

The invention claimed is:

1. A security inspection apparatus comprising:
 a radiation emitting device,
 a back-scatter detector located between the radiation emitting device and an inspected object,
 a size-distance detecting device located between the radiation emitting device and the inspected object, for detecting a height of the inspected object and a distance from the inspected object, and
 an orientation adjusting device for adjusting an orientation of the radiation emitting device according to the height of the inspected object and the distance between the inspected object and the size-distance detecting device.

2. The apparatus according to claim 1, wherein the orientation adjusting device further adjusts an angle of the back-scatter detector according to the orientation of the radiation emitting device.

3. The apparatus according to claim 2, wherein the orientation adjusting device adjusts an angle of the back-scatter detector, according to a height and an emission angle of the radiation emitting device, or
 determines an ideal angle of the back-scatter detector from the height and the emission angle of the radiation emitting device, and adjusts the angle of the back-scatter detector according to the ideal angle.

4. The apparatus according to claim 2, wherein the back-scatter detector is arc-shaped.

5. The apparatus according to claim 1, wherein the size-distance detecting device comprises a plurality of sensors for determining the height of the inspected object by judging a height of an obstacle in front of the sensors.

6. The apparatus according to claim 5, wherein the size-distance detecting device further comprises
  a camera located on a perpendicular bisector of the security inspection apparatus and the inspected object in a horizontal plane, and shoots in the direction of the perpendicular bisector;
  a calculating device acquires an image height of the inspected object and an image distance between the inspected object and the size-distance detecting device in a video image shot by the camera, and determines a distance between the inspected object and the size-distance detecting device from a ratio of the image distance to the image height and the height of the inspected object detected by the sensors.

7. The apparatus according to claim 1, wherein
  the orientation adjusting device adjusts a height and an emission angle of the radiation emitting device, according to the height of the inspected object and/or the distance between the inspected object and the size-distance detecting device; and/or
  the orientation adjusting device adjusts a distance between the radiation emitting device and the inspected object, according to the height of the inspected object and/or the distance between the inspected object and the size-distance detecting device.

8. The apparatus according to claim 1, wherein
  the orientation adjusting device determines an ideal height and an ideal emission angle of the radiation emitting device based on a predetermined strategy, from the height of the inspected object and/or the distance between the inspected object and the size-distance detecting device, and adjusts the height and the emission angle of the radiation emitting device according to the ideal height and the ideal emission angle; and/or
  the orientation adjusting device determines an ideal distance between the radiation emitting device and the inspected object based on a predetermined strategy, from the height of the inspected object and/or the distance between the inspected object and the size-distance detecting device, and adjusts the distance between the radiation emitting device and the inspected object according to the ideal distance.

9. The apparatus according to claim 1, wherein the radiation emitting device comprises:
  a ray source located in a center of the radiation emitting device; and
  a spatial modulator located between the ray source and the back-scatter detector, comprising a fixed shielding plate and a rotating shielding plate which is located between the inspected object and the fixed shielding plate, and comprises more than one hole.

10. The apparatus according to claim 1, further comprising a transportation facility for carrying and moving the security inspection apparatus;
  a control device for manually controlling the orientation adjusting device to perform the adjusting operation according to detection needs; and/or,
  a processor for receiving detection signals from the back-scatter detector.

11. A security inspection method comprising:
  acquiring a height of an inspected object and a distance between the inspected object and a size-distance detecting device by the size-distance detecting device;
  adjusting an orientation of a radiation emitting device according to the height of the inspected object and the distance between the inspected object and the size-distance detecting device;
  emitting X-rays towards the inspected object, and acquiring backscatter detection data by a back-scatter detector; and
  acquiring a detection result based on the backscatter detection data.

12. The method according to claim 11, further comprising:
  adjusting an angle of the back-scatter detector according to the orientation of the radiation emitting device.

13. The method according to claim 12, wherein adjusting an angle of the back-scatter detector according to the orientation of the radiation emitting device further comprises:
  adjusting the angle of the back-scatter detector according to a height and an emission angle of the radiation emitting device; or
  determining an ideal angle of the back-scatter detector from the height and the emission angle of the radiation emitting device, and adjusting the angle of the back-scatter detector according to the ideal angle.

14. The method according to claim 12, further comprising:
  manually adjusting the orientation of the radiation emitting device and/or the angle of the back-scatter detector according to detection needs.

15. The method according to claim 14, wherein manually adjusting the orientation of the radiation emitting device and/or the angle of the back-scatter detector according to detection needs comprises: manually adjusting the orientation of the radiation emitting device and/or the angle of the back-scatter detector for many times according to detection needs;
  acquiring backscatter detection data by a back-scatter detector comprises acquiring backscatter detection data after each time adjusting the orientation of the radiation emitting device and the angle of the back-scatter detector; and
  acquiring a detection result based on the backscatter detection data comprises: making a comprehensive analysis of the backscatter detection data acquired each time to determine the detection result.

16. The method according to claim 11, wherein acquiring a height of an inspected object comprises:
  the height of the inspected object is acquired by using a plurality of sensors to determine a height of an obstacle in front of the sensors.

17. The method according to claim 16, wherein acquiring a distance between the inspected object and the size-distance detecting device comprises:
  a video image is acquired by using a camera located on a perpendicular bisector of a security inspection apparatus and the inspected object in a horizontal plane, and shooting in the direction of the perpendicular bisector;
  acquiring an image height of the inspected object and an image distance between the inspected object and the size-distance detecting device in the video image, and determining a distance between the inspected object and the size-distance detecting device from a ratio of the image distance to the image height and the height of the inspected object.

18. The method according to claim 11, wherein adjusting the orientation of the radiation emitting device according to the height of the inspected object and the distance between the inspected object and the size-distance detecting device further comprises:
  adjusting a height and a emission angle of the radiation emitting device, according to the height of the inspected object and/or the distance between the inspected object and the size-distance detecting device; and/or
  adjusting the distance between the radiation emitting device and the inspected object, according to the height of the inspected object and the distance between the inspected object and the size-distance detecting device.

19. The method according to claim 11, wherein adjusting the orientation of the radiation emitting device according to the height of the inspected object and the distance between the inspected object and the size-distance detecting device further comprises:
  determining an ideal height and an ideal emission angle of the radiation emitting device based on a predetermined strategy, from the height of the inspected object and/or the distance between the inspected object and the size-distance detecting device, and adjusting the height and the emission angle of the radiation emitting device according to the ideal height and the ideal emission angle; and/or
  determining an ideal distance between the radiation emitting device and the inspected object using a predetermined strategy from the height of the inspected object and/or the distance between the inspected object and the size-distance detecting device, and adjusting the distance between the radiation emitting device and the inspected object according to the ideal distance.

* * * * *